(12) United States Patent
Van Dalen et al.

(10) Patent No.: US 8,308,296 B2
(45) Date of Patent: Nov. 13, 2012

(54) VISION TESTING APPARATUS AND METHOD

(75) Inventors: Johan T. W. Van Dalen, Tucson, AZ (US); Dan D. Carda, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 78 days.

(21) Appl. No.: 12/396,387

(22) Filed: Mar. 2, 2009

(65) Prior Publication Data
US 2009/0219482 A1    Sep. 3, 2009

Related U.S. Application Data

(60) Provisional application No. 61/032,843, filed on Feb. 29, 2008.

(51) Int. Cl.
*A61B 3/08* (2006.01)
*A61B 3/10* (2006.01)

(52) U.S. Cl. ........................................ 351/201; 351/221

(58) Field of Classification Search .................. 351/201, 351/221
See application file for complete search history.

(56) References Cited

U.S. PATENT DOCUMENTS

| | | | |
|---|---|---|---|
| 2,477,516 A | 7/1949 | Haas | |
| 5,047,049 A | 9/1991 | Salai | |
| 5,550,719 A * | 8/1996 | Kuo | ............................... 362/120 |
| 5,685,637 A | 11/1997 | Chapman et al. | |
| 6,357,893 B1 | 3/2002 | Belliveau | |
| 2006/0241970 A1 | 10/2006 | Winarski | |
| 2007/0223213 A1 | 9/2007 | Bassi et al. | |

FOREIGN PATENT DOCUMENTS
GB    2105057    0/1893

OTHER PUBLICATIONS

International Preliminary Report on Patentability dated Nov. 12, 2010.

* cited by examiner

*Primary Examiner* — Ricky Mack
*Assistant Examiner* — Mahidere Sahle
(74) *Attorney, Agent, or Firm* — Dale F. Regelman; Quarles & Brady LLP (57) ABSTRACT

A testing device and method are presented for detecting binocular vision problems in patients. The testing device includes a body with a flat portion disposed along one side. Extending outwardly from the top of the body is an actuating means. The device further includes a first set of lights disposed on the surface of the device a first distance away from a center point and a second set of lights disposed a second distance away from the center point. Each of the lights in the first set are smaller than each of the lights in the second set. Further, the second distance is shorter than the first distance.

13 Claims, 6 Drawing Sheets

VISION TESTING APPARATUS AND METHOD

RELATED APPLICATIONS

This patent application claims priority to prior copending provisional Application No. 61/032,843 filed Feb. 29, 2008, entitled Vision Testing Apparatus and Method, which is hereby incorporated herein by reference.

BACKGROUND

The present invention relates generally to testing devices and procedures for binocular vision, and more particularly to those utilizing the Worth 4-dot test.

Binocular vision is the ability to maintain visual focus on an object with both eyes, creating a single visual image. When the brain fails to process the visual input received by one or the other of the eyes properly, one of the images may be suppressed causing a patient to experience distortions in depth perception and visual measurement of distance. Alternatively, the brain may fuse the images, causing the patient to suffer from double vision.

The loss of binocularity is primarily seen in patients with strabismus, with or without amblyopia.

SUMMARY

In one implementation, a device for testing for binocular vision is presented. The device includes a body having a flat portion along one side and an actuating means that extends outwardly from the top. The device further includes a first set of lights disposed on the surface of the device a first distance away from a center point.

In another implementation, a device for testing for binocular vision is presented. The device includes a body having a flat portion along one side and an actuating means that extends outwardly from the top. The device further includes a first set of lights disposed on the surface of the device a first distance away from a center point and a second set of lights disposed a second distance away from the center point. Each of the lights in the first set are smaller than each of the lights in the second set. Further, the second distance is shorter than the first distance.

Another implementation, a method of detecting binocular vision problems in a patient is presented. The method includes the use of a testing device having multiple lights disposed on a surface. The testing device is further capable of powering the lights at a plurality of brightness settings. The method includes supplying a pair of test glasses to the patient having different lenses. Next a first brightness setting is selected and the lights are exposed to the patient at the brightness setting. Finally, a result is determined.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

One test used to examine a patient's binocular vision is the "Worth 4-dot" test, also known as the "Worth dot" test. During the Worth 4-dot test, the patient wears anaglyphic glasses. Such glasses have one red lens, typically over the right eye, and one green lens, typically over the left eye. The patient is then shown a modified flashlight where the front is covered such that light is emitted only through four holes arranged in a diamond pattern. When the modified flashlight is positioned correctly, the top hole shows only red light, the left and right holes show only green light, and the bottom hole shows only white light.

The red lens of the anaglyphic glasses blocks the green light and the green lens blocks the red light, making it possible to determine if the patient is using both eyes simultaneously in a coordinated manner. When both eyes are open, a patient having normal vision will see all four lights. When the patient closes one eye, they will see either two or three lights depending on which eye is suppressed. If the patient suffers from diplopia (double vision) vision, he/she will see five lights.

One limitation of performing a Worth 4-dot test using a modified flashlight is that the flashlight must be positioned properly for the test to be accurate. Given a flashlight's uniform shape, it is easy for the test administrator to rotate the flashlight such that the holes are no longer positioned correctly, thereby giving inaccurate test results. Further, a flashlight can be cumbersome for the test administrator.

Another limitation of using the described flashlight to test for binocular vision is that it has only one power level and therefore one brightness setting. This can make it difficult, if not impossible, to quantify the degree of binocular vision the patient suffers from. Further, most flashlights are powered with D cell batteries that weaken over time, causing the power level, and therefore the brightness, to fluctuate in an uncontrolled manner.

Figure 1A:
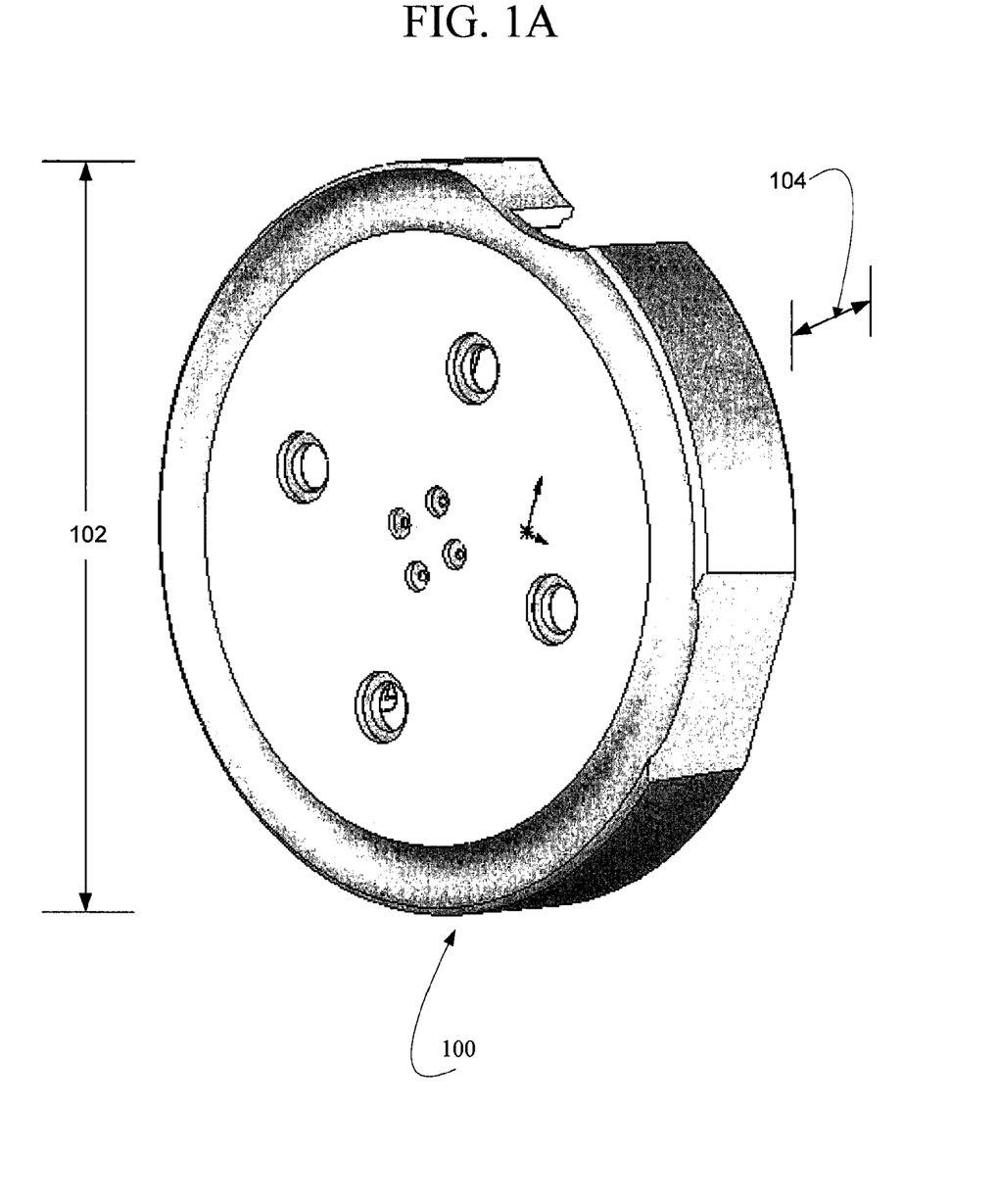
FIG. 1A depicts a perspective view of an exemplary embodiment of Applicants' test apparatus.
Figure 1B:
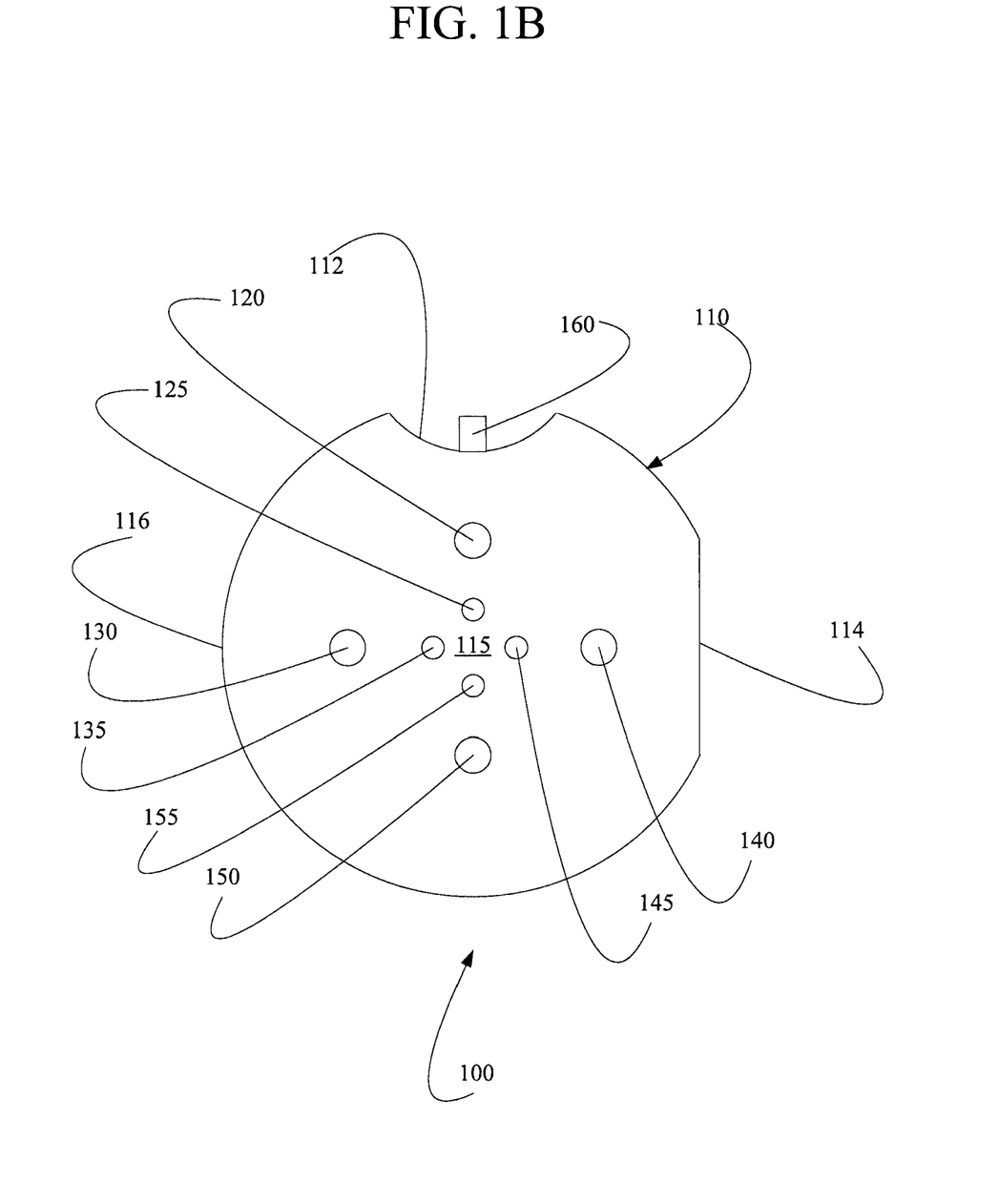
FIG. 1B depicts a front view of an exemplary embodiment of Applicants' test apparatus.

In the illustrated embodiment of FIGS. 1A and 1B, Applicants' test apparatus 100 comprises a cylindrical housing 110 comprising a first end comprising a first surface 115 comprising a center point, and a second end comprising a second surface, wherein said cylindrical body is formed to include a flat portion 114 disposed between said first surface and said second surface. In certain embodiments, test apparatus 100 comprises a diameter 102 of between about 1.5 inches to about 3 inches. In certain embodiments, test apparatus 100 comprises a diameter 102 of about 2.5 inches. In certain embodiments, test apparatus 100 comprises a thickness 104 of between about 0.25 inches to about 1 inch. In certain embodiments, test apparatus 100 comprises a thickness 104 of about 0.5 inch.

Referring now to FIG. 1B, testing apparatus 100 further comprises an actuating means 160 extending outwardly through housing 110 and into recessed portion 112. In the illustrated embodiment of FIG. 1B, actuating means 160 comprises a push button. In other embodiments, actuating means 160 comprises a switch. In yet other embodiments, actuating means 160 is electronic. In yet other embodiments, actuating means 160 is mechanical.

In the illustrated embodiment of FIG. 1B, light emitting devices 120, 125, 130, 135, 140, 145, 150 and 155 are disposed on surface 115. In other embodiments, only light emitting devices 120, 130, 140, and 150 are disposed on surface 115. In certain embodiments, light emitting devices 120, 125, 130, 135, 140, 145, 150 and 155 comprise light emitting diodes ("LEDs"). In certain embodiments, light emitting devices 120 and 125, when active, emit red light. In certain embodiments, light emitting devices 130 and 135, when active, emit green light. In certain embodiments, light emitting devices 140 and 145, when active, emit green light. In certain embodiments, light emitting devices 150 and 155, when active, emit white light.

In the illustrated embodiment of FIG. 1B, light emitting devices 125, 135, 145, and 155 are located at first distance and light emitting devices 120, 130, 140, and 150 are located at a second distance from a center point on surface 115. In certain embodiments, the first distance is one-quarter of the second distance. In certain embodiments, the first distance is 0.5 inch. In certain embodiments, the second distance is 1.5 inches.

A correct orientation of the colors displayed by the plurality of light emitting devices 120, 125, 130, 135, 140, 145, 150 and 155 is critical to proper use. Housing 110 is shaped such that test device can be held in a user's right hand, with the thumb or palm resting on flat portion 114, and an index or middle finger positioned on actuating means 160. When holding test apparatus in either hand, if flat portion 114 is vertical, then test apparatus is correctly oriented such that the plurality of light emitting devices 120, 125, 130, 135, 140, 145, 150 and 155 are viewed by the test subject, i.e. a patient, with the red light-emitting devices at the top and the white light-emitting devices at the bottom.

Figure 2A:
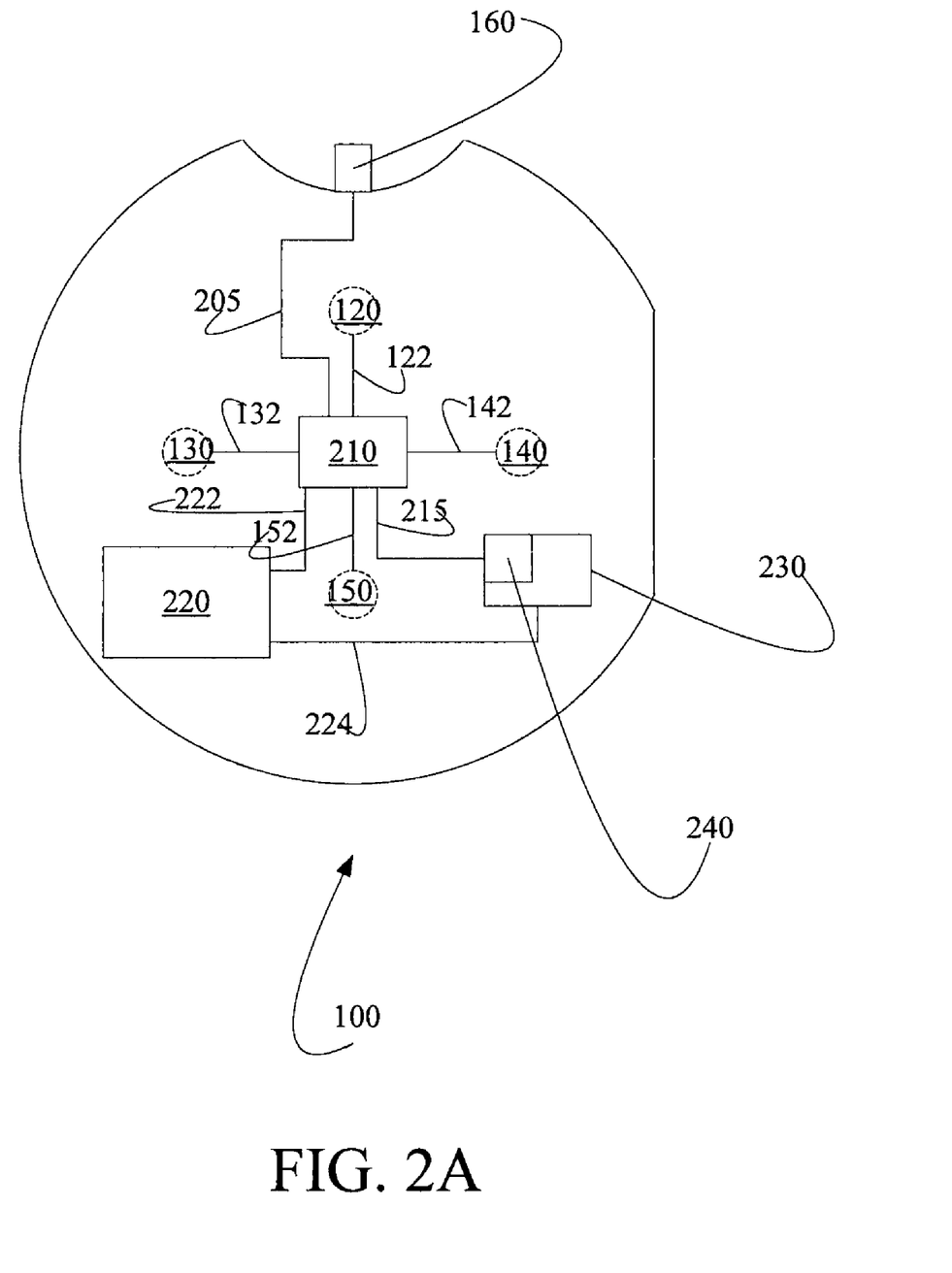
FIGS. 2A and 2B are block diagrams showing exemplary embodiments of the components of Applicants' test apparatus.

Referring to FIG. 2A, in certain embodiments test apparatus 100 further comprises processor 210, power source 220, computer readable medium 230, and computer readable program code 240. Processor 210 utilizes instructions 240 to operate test apparatus 100. Processor 210 is interconnected with actuating means 160 via communication link 205 and with memory 230 via communication link 215.

In certain embodiments, processor 210, memory 230, and instructions 240, comprise an integral assembly. In certain embodiments, processor 210, memory 230, and instructions 240, comprise an application specific integrated circuit ("ASIC").

Power source 220 supplies power to processor 210 and memory 230 via power buses 222 and 224, respectively. Processor 210 is interconnected to light emitting device 120 via power bus 122. Processor 210 is interconnected to light emitting device 130 via power bus 132. Processor 210 is interconnected to light emitting device 140 via power bus 142. Processor 210 is interconnected to light emitting device 150 via power bus 152. When actuating means 160 is depressed to a first actuating point, processor 210 supplies power to light emitting devices 120, 130, 140, and 150.

Instructions 240 comprise power levels for (N) different brightness levels. Using a brightness level of 1, processor 210 supplies the smallest amount of power to light emitting devices 120, 130, 140, and 150. Using the (N)th brightness level, processor 210 supplies the greatest amount of power to light emitting devices 120, 130, 140, and 150. In embodiments wherein light emitting devices 120, 130, 140, and 150, comprise LEDs, processor 210 varies the current supplied to those LEDS as a function of (i), wherein (i) is greater than or equal to 1 and less than or equal to (N).

Figure 2B:
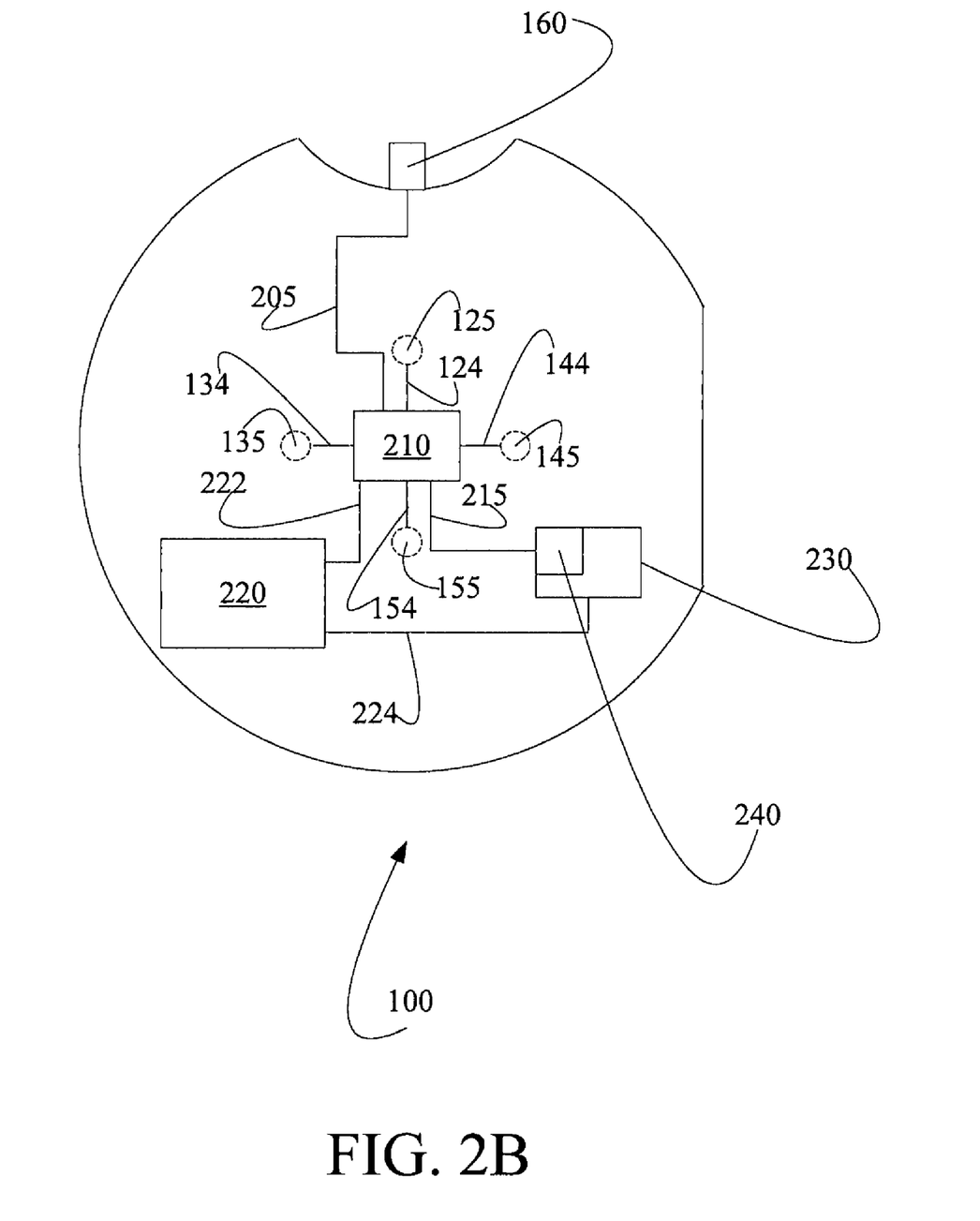

Referring to FIG. 2B, in certain embodiments, processor 210 is interconnected to light emitting device 125 via power bus 124. Processor 210 is interconnected to light emitting device 135 via power bus 134. Processor 210 is interconnected to light emitting device 145 via power bus 144. Processor 210 is interconnected to light emitting device 155 via power bus 154. When actuating means 160 is depressed to a second actuating point, processor 210 supplies power to light emitting devices 125, 135, 145, and 155.

Instructions 240 further comprise power levels for (P) different brightness levels. Using a brightness level of 1, processor 210 supplies the smallest amount of power to light emitting devices 125, 135, 145, and 155. Using the (P)th brightness level, processor 210 supplies the greatest amount of power to light emitting devices 125, 135, 145, and 155. In embodiments wherein light emitting devices 125, 135, 145, and 155, comprise LEDs, processor 210 varies the current supplied to those LEDS as a function of (j), wherein (j) is greater than or equal to 1 and less than or equal to (P).

Figure 3A:
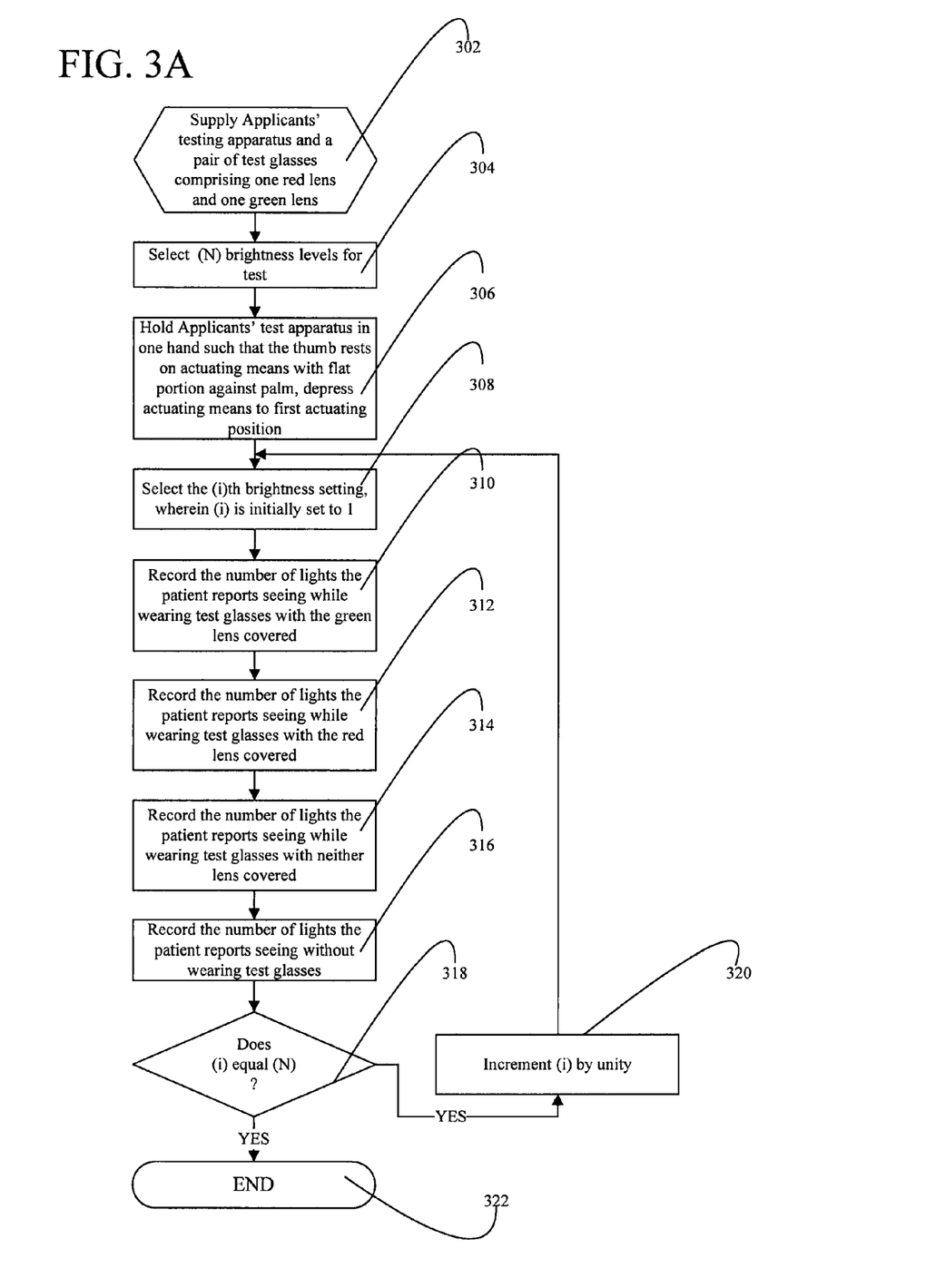
FIGS. 3A and 3B are flow charts summarizing exemplary vision tests administered using Applicants' test apparatus.

FIG. 3A summarizes the steps of an exemplary vision test administered to a patient using Applicants' test apparatus 100. Referring now to FIG. 3A, in step 302 the method supplies Applicants' test apparatus 100 and a pair of test glasses comprising one red lens and one green lens, wherein the red lens covers the patient's right eye and the green lens covers the patient's left eye.

In step 304, the method selects the number of brightness levels to employ. In certain embodiments, (N) is one. In these embodiments, Applicant's apparatus 100 does not comprise a processor or memory. Rather in the (N)=1 embodiments, the actuating means 160 comprises a switch which, when depressed to a first actuating position, supplies power to each of light emitting devices 120, 130, 140, and 150.

In embodiments wherein test apparatus 100 comprises a processor and memory, and wherein (N) is greater than 1, the tester can elect to only use one of those (N) brightness levels. In these embodiments, the tester first repeatedly depresses actuating means 160 to the first actuating position until the desired brightness level is reached.

In step 306, the tester holds test apparatus 100 in one hand as described hereinabove and depresses actuating means 160 to the first actuating position. In step 308, the tester selects an (i)th brightness setting, wherein (i) is initially set to one.

In one embodiment, the tester holds the test apparatus forty-five (45) centimeters from the patient. In other embodiment, the tester varies the distance the test apparatus is from the patient to access the size of the area of suppression of the patient's visual field.

In step 310, the method records the number of lights the patient reports seeing while wearing the test glasses with the green lens covered. Using only the right eye seeing through the red lens, the patient should see two lights, namely the red light and the white light.

In step 312, the method records the number of lights the patient reports seeing while wearing the test glasses with the red lens covered. Using only the left eye seeing through the green lens, the patient should see three lights, namely the two green lights and the white light.

In step 314, the method records the number of lights the patient reports seeing while wearing the test glasses with neither lens covered. Using both eyes, the patient should see all four lights.

In step 316, the method records the number of lights the patient reports seeing without the test glasses. With both eyes open and no test glasses, the patient should see four lights if the patient has focused binocular vision. If the patient sees 5 lights using both eyes, then the patient does not have proper binocular vision, and likely suffers from double vision.

In step 318, the method determines if all the brightness levels have been tested, i.e. if (i) equals (N). If all brightness levels have been tested, then the method transitions from step 318 to step 322 and ends. Alternatively, if the method determines in step 318 that (i) does not equal (N), then the method transitions from step 318 to step 320 wherein (i) is incremented by unity, i.e. (i) is set to (i+1). The method transitions from step 320 to step 308 and continues as described herein. In certain embodiments, steps 320 and 322 comprise depressing actuating means 160 to a first actuating position, wherein processor 210 increases the power supplied to each of light emitting devices 120, 130, 140, and 150.

Figure 3B:
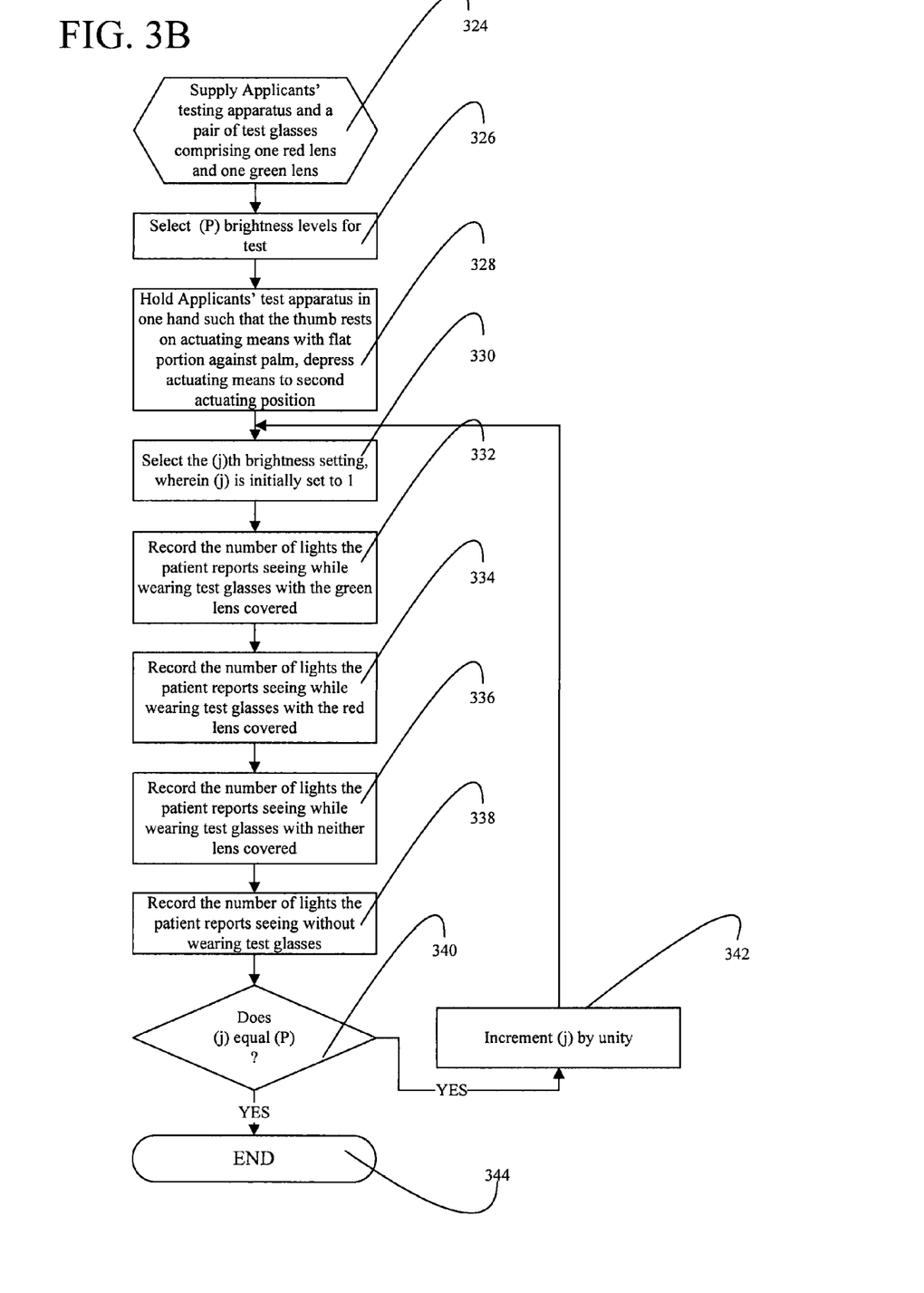

FIG. 3B summarizes the steps of another exemplary vision test administered to a patient using Applicants' test apparatus 100. Referring now to FIG. 3B, in step 324 the method supplies Applicants' test apparatus 100 and a pair of test glasses comprising one red lens and one green lens, wherein the red lens covers the patient's right eye and the green lens covers the patient's left eye.

In step 326, the method selects the number of brightness levels to employ. In certain embodiments, (P) is one. In these embodiments, Applicant's apparatus 100 does not comprise a processor or memory. Rather in the (P)=1 embodiments, the actuating means 160 comprises a switch which, when depressed to a second actuating position, supplies power to each of light emitting devices 125, 135, 145, and 155.

In embodiments wherein test apparatus 100 comprises a processor and memory, and wherein (P) is greater than 1, the tester can elect to only use one of those (P) brightness levels. In these embodiments, the tester first repeatedly depresses actuating means 160 to the second actuating position until the desired brightness level is reached.

In step 328, the tester holds test apparatus 100 in one hand as described hereinabove and depresses actuating means 160 to the second actuating position. In step 330, the tester selects an (j)th brightness setting, wherein (j) is initially set to one.

In one embodiment, the tester holds the test apparatus at approximately twenty-five (25) centimeters from patient to drive the patient's eyes together to see the same object.

In step 332, the method records the number of lights the patient reports seeing while wearing the test glasses with the green lens covered. Using only the right eye seeing through the red lens, the patient should see two lights, namely the red light and the white light.

In step 334, the method records the number of lights the patient reports seeing while wearing the test glasses with the red lens covered. Using only the left eye seeing through the green lens, the patient should see three lights, namely the two green lights and the white light.

In step 336, the method records the number of lights the patient reports seeing while wearing the test glasses with neither lens covered. Using both eyes, the patient should see all four lights.

In step 338, the method records the number of lights the patient reports seeing without the test glasses. With both eyes open and no test glasses, the patient should see four lights if the patient has focused binocular vision. If the patient sees 5 lights using both eyes, the patient's suffers from double vision.

In step 340, the method determines if all the brightness levels have been tested, i.e. if (j) equals (P). If all brightness levels have been tested, then the method transitions from step 340 to step 344 and ends. Alternatively, if the method determines in step 340 that (j) does not equal (P), then the method transitions from step 340 to step 342 wherein (j) is incremented by unity, i.e. (j) is set to (j+1). The method transitions from step 342 to step 330 and continues as described herein. In certain embodiments, steps 342 and 344 comprise depressing actuating means 160 to a second actuating position, wherein processor 210 increases the power supplied to each of light emitting devices 125, 135, 145, and 155.

In certain embodiments, individual steps recited in FIGS. 3 and 4, may be combined, eliminated, or reordered.

In certain embodiments, Applicants' invention includes instructions, such as computer readable program code 240 (FIG. 2A), residing in computer readable medium, such as for example computer readable medium 230 (FIG. 2A) wherein those instructions are executed by a processor, such as processor 210 (FIG. 2A), to perform one or more of steps recited in FIG. 3A, and/or one or more of steps recited in FIG. 3B.

While the preferred embodiments of the present invention have been illustrated in detail, it should be apparent that modifications and adaptations to those embodiments may occur to one skilled in the art without departing from the scope of the present invention.

What is claimed is:

1. A testing device for binocular vision, comprising:
    a cylindrical body comprising a first end comprising a first surface comprising a center point, and a second end comprising a second surface, wherein said cylindrical body is formed to include a flat portion disposed between said first surface and said second surface;
    an actuating means extending outwardly from said body;
    four first light-emitting devices configured to emit light in the visible spectrum and disposed on said first surface, wherein each of said four first light-emitting devices is disposed a first distance from said center point; and
    four second light-emitting devices light-emitting devices configured to emit light in the visible spectrum and disposed on said first surface, wherein each of said four second plurality of light-emitting devices is disposed a second distance from said center point;

wherein:
each first light-emitting device is circular and comprises a first diameter;
each second light-emitting device is circular and comprises a second diameter;
said second diameter is less than said first diameter;
said testing device is configured to test for binocular vision.

2. The device of claim 1, wherein the second distance is less than the first distance.

3. The device of claim 1, wherein when the actuating means is in a first actuating position the light-emitting devices are energized, and wherein when the actuating means is in a second actuating position the second plurality of light-emitting devices are energized.

4. The device of claim 1, further comprising:
a processor interconnected to said actuating means;
a computer readable medium interconnected to said processor;
computer readable program code encoded in said computer readable medium; and
a power source interconnected to said processor and said computer readable medium.

5. The device of claim 1, wherein:
the first plurality of light-emitting devices are interconnected to said processor;
the second plurality of light-emitting devices are interconnected to said processor;
the first plurality of light-emitting devices comprise light emitting diodes ("LEDs");
the second plurality of light-emitting devices comprise light emitting diodes ("LEDs").

6. The device of claim 1, wherein:
said body is formed to include a recessed portion;
said actuating means extends outwardly through said body and into said recessed portion.

7. The device of claim 1, wherein the actuating means comprises a push button.

8. A method of detecting binocular vision problems in a patient, comprising:
supplying a testing device comprising a cylindrical body comprising a first end comprising a first surface comprising a center point, and a second end comprising a second surface, wherein said cylindrical body is formed to include a flat portion disposed between said first surface and said second surface, an actuating means extending outwardly from said body, four first light-emitting devices configured to emit light in the visible spectrum and disposed on said first surface, wherein each of said four first light-emitting devices is disposed a first distance from said center point, and four second light-emitting devices light-emitting devices configured to emit light in the visible spectrum and disposed on said first surface, wherein each of said four second plurality of light-emitting devices is disposed a second distance from said center point, wherein each first light-emitting device is circular and comprises a first diameter, each second light-emitting device is circular and comprises a second diameter, and said second diameter is less than said first diameter;
instructing a patient to wear a pair of test glasses comprising a first lens comprising a first color and a second lens comprising a second color, wherein the first color and the second color differ;
holding said testing device in one hand such that said flat portion rests against a thumb and such that a forefinger rests upon said actuating means, such that a top light-emitting device emits a red light when energized, two middle light-emitting devices each emit a green color when energized, and a bottom light-emitting device emits a white color when energized;
energizing said first plurality of light-emitting devices at a first brightness level;
directing said first surface toward said patient; and
detecting whether the patient has binocular vision problems.

9. The method of claim 8, further comprising:
recording a number of lights seen with the first lens covered;
recording a number of lights seen with the second lens covered;
recording a number of lights seen with neither lens covered; and
recording a number of lights seen without the test glasses.

10. The method of claim 9, further comprising
energizing said first plurality of light-emitting devices at a second brightness level, wherein said second brightness level is greater than said first brightness level; and
repeating said recording steps.

11. The method of claim 8, wherein:
the first plurality of light-emitting devices are energized for a first time interval;
the second plurality of light-emitting devices are energized for a second time interval;
said first time interval differs from said second time interval.

12. The method of claim 11, wherein the first plurality of light-emitting devices are positioned a distance of about forty-five (45) centimeters from said patient.

13. The method of claim 11, wherein the first plurality of light-emitting devices are positioned a distance of about twenty-five (25) centimeters from said patient.

* * * * *